(12) United States Patent
Meyer et al.

(10) Patent No.: US 12,168,101 B2
(45) Date of Patent: Dec. 17, 2024

(54) AROMATHERAPY SENSORY TOOL

(71) Applicants: Pam Renee Meyer, Rio Rancho, NM (US); Lee Anna Marie Maestas, Albuquerque, NM (US)

(72) Inventors: Pam Renee Meyer, Rio Rancho, NM (US); Lee Anna Marie Maestas, Albuquerque, NM (US)

( * ) Notice: Subject to any disclaimer, the term of this patent is extended or adjusted under 35 U.S.C. 154(b) by 922 days.

(21) Appl. No.: 17/200,580

(22) Filed: Mar. 12, 2021

(65) Prior Publication Data

US 2021/0283365 A1  Sep. 16, 2021

Related U.S. Application Data

(60) Provisional application No. 62/988,808, filed on Mar. 12, 2020.

(51) Int. Cl.
| | |
|---|---|
| *A61L 9/12* | (2006.01) |
| *A44C 15/00* | (2006.01) |
| *A61M 21/02* | (2006.01) |
| *A61M 21/00* | (2006.01) |

(52) U.S. Cl.
CPC .......... *A61M 21/02* (2013.01); *A44C 15/002* (2013.01); *A61L 9/12* (2013.01); *A61L 2209/15* (2013.01); *A61M 2021/0016* (2013.01); *A61M 2021/0022* (2013.01); *A61M 2209/08* (2013.01)

(58) Field of Classification Search
CPC .......... A61L 9/04; A61L 9/12; A61L 2209/15; A61M 16/208; A61M 21/00; A61M 21/02; A61M 2021/0016; A61M 2021/0022; A61M 2209/08; A44C 15/002

USPC .................................. 239/36, 44, 53, 55–57
See application file for complete search history.

(56) References Cited

U.S. PATENT DOCUMENTS

| | | | | |
|---|---|---|---|---|
| 2,025,657 | A * | 12/1935 | Ganz ...................... | A45D 37/00 D11/40 |
| 6,123,946 | A | 9/2000 | Wei | |
| 7,815,878 | B1 * | 10/2010 | Wheatley ............... | A63B 43/00 422/123 |
| 2009/0148483 | A1 * | 6/2009 | Rashid ................... | A61Q 13/00 424/443 |

(Continued)

OTHER PUBLICATIONS

DIY Aromatherapy Rice Bag, https://pistachioproject.com/2014/12/diy-aromatherapy-rice-bag.html.

*Primary Examiner* — Darren W Gorman (57) ABSTRACT

An aromatherapy sensory tool is designed for users to help self-regulate the body, emotions, and feelings of stress/anxiety or other emotions. The aromatherapy sensory tool includes an outer gas-permeable enclosure, an inner gas-permeable enclosure, a quantity of absorbent filling, and a quantity of aromatherapy fluid. When in use, the outer gas-permeable enclosure prevents the leak of the quantity of aromatherapy fluid while allowing the smell of the quantity of aromatherapy fluid pass through and reach the user. The inner gas-permeable enclosure is designed to contain the quantity of absorbent filling within the outer gas-permeable enclosure. Similarly, the inner gas-permeable enclosure prevents the leak of the quantity of aromatherapy fluid while allowing the smell of the quantity of aromatherapy fluid to exit out of the outer gas-permeable enclosure. The quantity of absorbent filling retains the quantity of aromatherapy fluid and diffuses the quantity of aromatherapy fluid for aromatherapy purposes.

15 Claims, 10 Drawing Sheets

(56) References Cited

U.S. PATENT DOCUMENTS

2013/0013036 A1    1/2013  Zaragosa
2018/0311394 A1*  11/2018  Cutler .................... A61L 9/12
2019/0125915 A1*   5/2019  Roszell ................. A61L 9/014

* cited by examiner

AROMATHERAPY SENSORY TOOL

The current application claims a priority to U.S. provisional application Ser. No. 62/988,808 filed on Mar. 12, 2020.

FIELD OF THE INVENTION

The present invention generally relates to therapeutic devices and aromatherapy systems. More specifically, the present invention provides an aromatherapy sensory tool for all ages designed to help manage feelings of stress/anxiety and other emotions.

BACKGROUND OF THE INVENTION

An objective of the present invention is to provide a FEELING FRIEND, an aromatherapy sensory tool for all ages specifically designed for children and adolescents to help manage feelings of stress/anxiety, sadness, anger, overexcitement, etc. The present invention helps young users self-regulate their body and emotions anywhere, such as at home or school. The present invention includes an outer gas-permeable enclosure which can be made from various soft, furry, fuzzy, or nubby fabrics. The outer gas-permeable enclosure can be provided in different sizes appropriate for different ages. Further, the outer gas-permeable enclosure contains an inner gas-permeable enclosure that is preferably made from flannel. The inner gas-permeable enclosure is filled with a quantity of absorbent filling and the quantity of absorbent filling diffuses a quantity of aromatherapy fluid for aromatherapy purposes. The quantity of absorbent filling is preferably rice, but the quantity of absorbent filling may be another absorbent material such as, but not limited to, felt pads or polypropylene beads.

The inner gas-permeably enclosure is completely incased in the outer gas-permeable enclosure to ensure that the quantity of aromatherapy fluid does not get on the fingers of the user while being used. The outer gas-permeable enclosure is sewed shut with a bead anchored in a corner of the seam to allow the re-application of an additional quantity of aromatherapy fluid with a pipette. The pipette is inserted into the bead to apply the additional quantity of aromatherapy fluid into the inner gas-permeable enclosure. The bead can also be replaced with other fasteners such as a zipper, clasp, snap, hook and loop fasteners, etc. In addition, two safety eyes are attached through interfacing to middle center of one side of the outer gas-permeable enclosure. Additional ornamental features can be provided to customize the look of the present invention. Furthermore, the present invention can be carried on a lanyard, hook, or similar attachment device for ease of transportation.

DETAILED DESCRIPTION OF THE INVENTION

All illustrations of the drawings are for the purpose of describing selected versions of the present invention and are not intended to limit the scope of the present invention.

In reference to FIGS. 1 through 10, the present invention is an aromatherapy sensory tool. The present invention is designed for users to help self-regulate the body, emotions, and feelings of stress/anxiety or other emotions. The present invention may comprise an outer gas-permeable enclosure 1, an inner gas-permeable enclosure 4, a quantity of absorbent filling 7, and a quantity of aromatherapy fluid 8. The outer gas-permeable enclosure 1 is designed to facilitate the operation of the present invention with one or two hands for therapeutic purposes. The outer gas-permeable enclosure 1 prevents the leak of the quantity of aromatherapy fluid 8 while allowing the smell of the quantity of aromatherapy fluid 8 pass through and reach the user. The inner gas-permeable enclosure 4 is designed to contain the quantity of absorbent filling 7 within the outer gas-permeable enclosure 1. Similarly, the inner gas-permeable enclosure 4 prevents the leak of the quantity of aromatherapy fluid 8 while allowing the smell of the quantity of aromatherapy fluid 8 to exit out of the outer gas-permeable enclosure 1. The quantity of absorbent filling 7 retains the quantity of aromatherapy fluid 8 and diffuses the quantity of aromatherapy fluid 8 for aromatherapy purposes.

Figure 1:
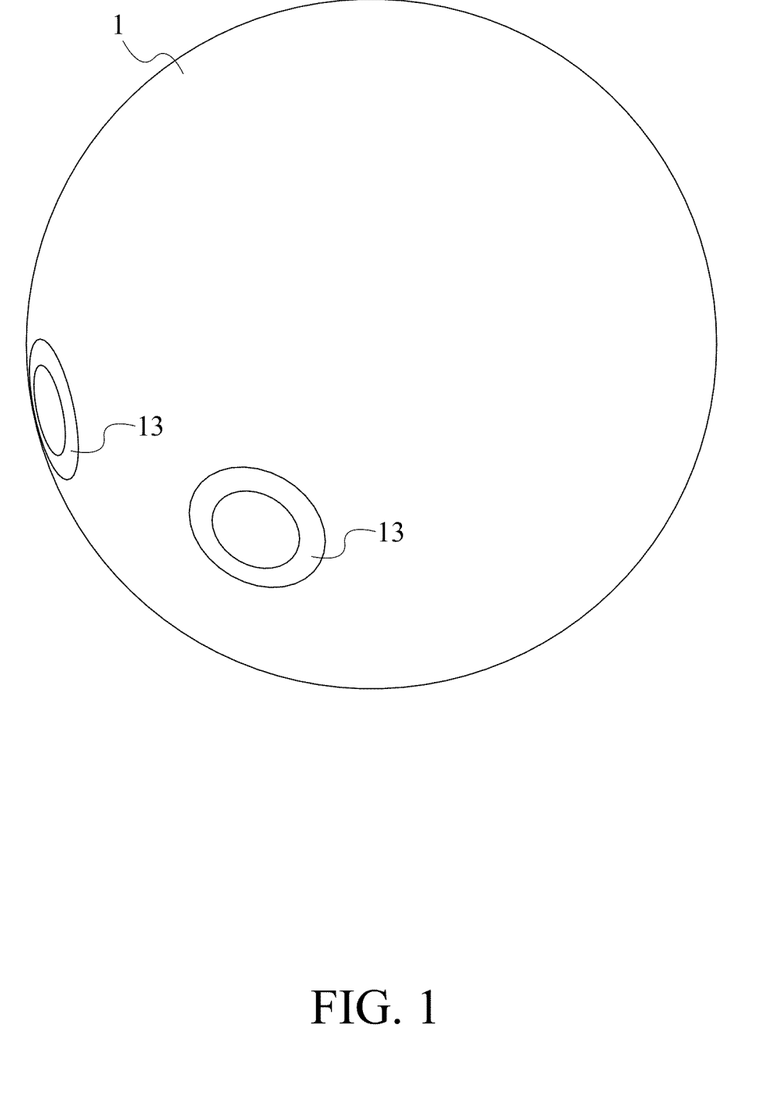
FIG. 1 is a top perspective view of the present invention.
Figure 2:
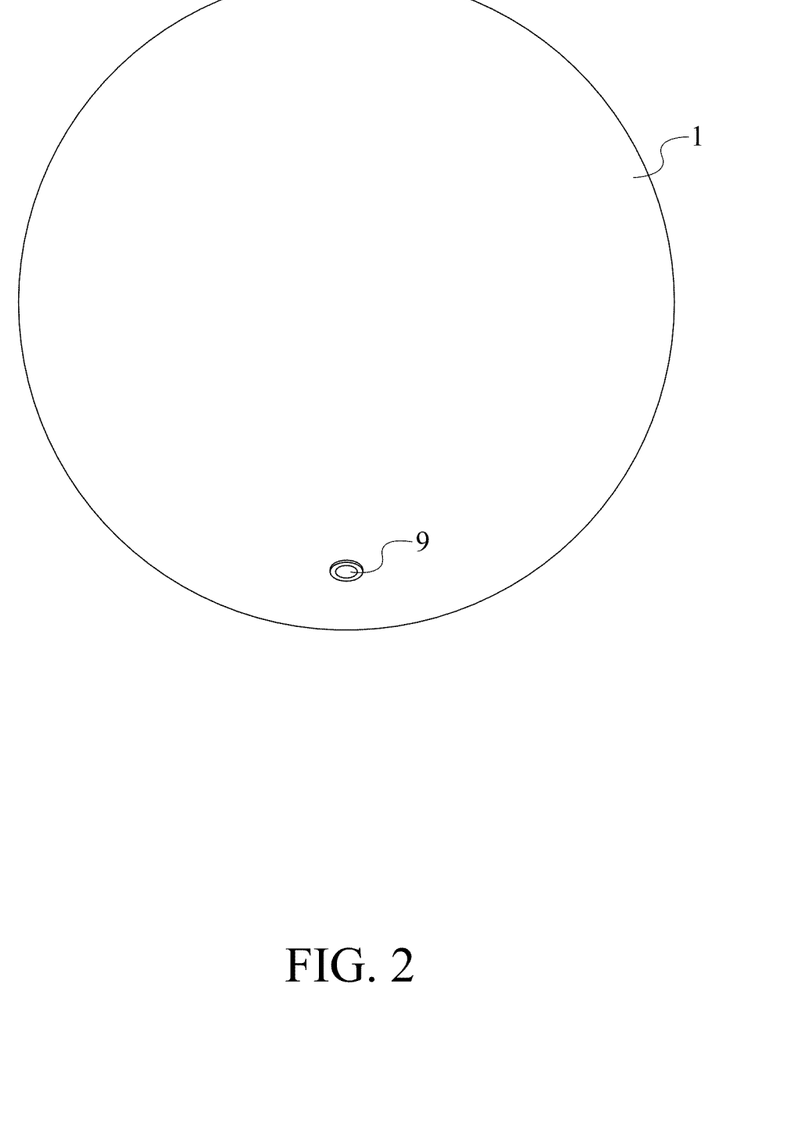
FIG. 2 is a bottom perspective view of the present invention displaying the one-way valve.
Figure 3:
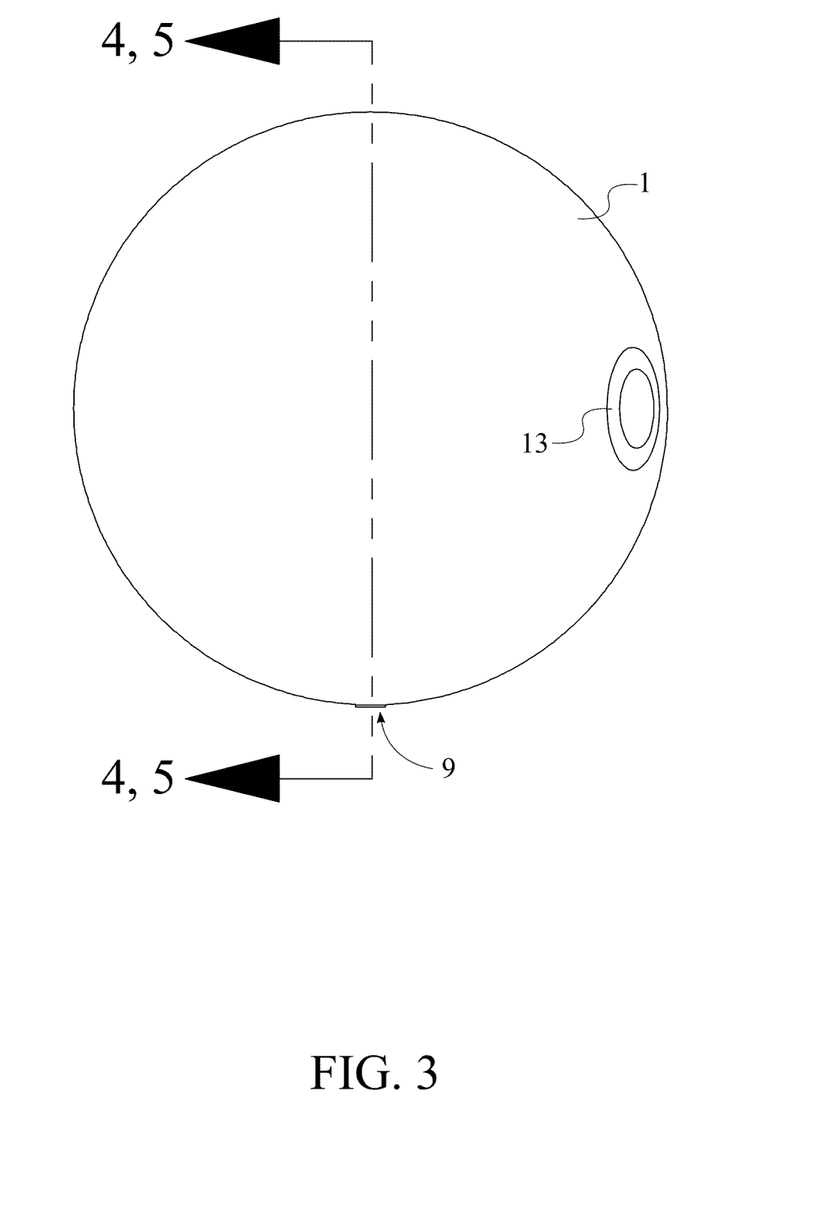
FIG. 3 is a side view of the present invention.

The general configuration of the aforementioned components enables users of any age to use the present invention to relieve stress/anxiety or other emotions through aromatherapy, anywhere and anytime. As can be seen in FIGS. 1-3, the outer gas-permeable enclosure 1 is preferably a spherical shape sized small enough to be held on one hand. The outer gas-permeable enclosure 1 is preferably made of a tactilely soft material. Further and as can be seen in FIG. 11, the outer gas-permeable enclosure 1 can be made from soft fabrics of various colors and textures such as smooth, fuzzy, furry, nubby, etc. The inner gas-permeable enclosure 4 is preferably made of a fabric material. More specifically, the inner gas-permeable enclosure 4 can be made of flannel material. The quantity of absorbent filling 7 is preferably rice or polypropylene beads. The quantity of aromatherapy fluid 8 is preferably an essential oil. The quantity of absorbent filling 7 is soaked with the quantity of aromatherapy fluid 8. In more detail, the quantity of absorbent filling 7 absorbs the quantity of aromatherapy fluid 8 in order to effectively retain the quantity of aromatherapy fluid 8. The quantity of absorbent filling 7, while soaked with the quantity of aromatherapy fluid 8, is positioned within the inner gas-permeable enclosure 4. This arrangement prevents any leak of the quantity of aromatherapy fluid 8. Moreover and with reference to FIG. 4, the inner gas-permeable enclosure 4 is positioned within the outer gas-permeable enclosure 1. This arrangement further prevents the leak of the quantity of aromatherapy fluid 8. The outer gas-permeable enclosure 1 and the inner gas-permeable enclosure 4 are two hollow spherical bodies and separated by a spherical gap 15. The outer gas-permeable enclosure 1, the inner gas-permeable enclosure 4, and the spherical gap 15 are positioned concentric with each other. The inner gas-permeable enclosure 4 can alternatively be stitched within the outer gas-permeable enclosure 1 in order to prevent the inner gas-permeable enclosure 4 from moving inside the outer gas-permeable enclosure 1. Furthermore, when the present invention is squeezed by the user, the quantity of absorbent filling 7 diffuses the quantity of aromatherapy fluid 8 through the inner gas-permeable enclosure 4 in order for the smell of the quantity of aromatherapy fluid 8 to be released out of the outer gas-permeable enclosure 1. Thus, the smell of the quantity of aromatherapy fluid 8 provides aromatherapy for the user to relieve stress, anxiety, or other emotions.

Figure 4:
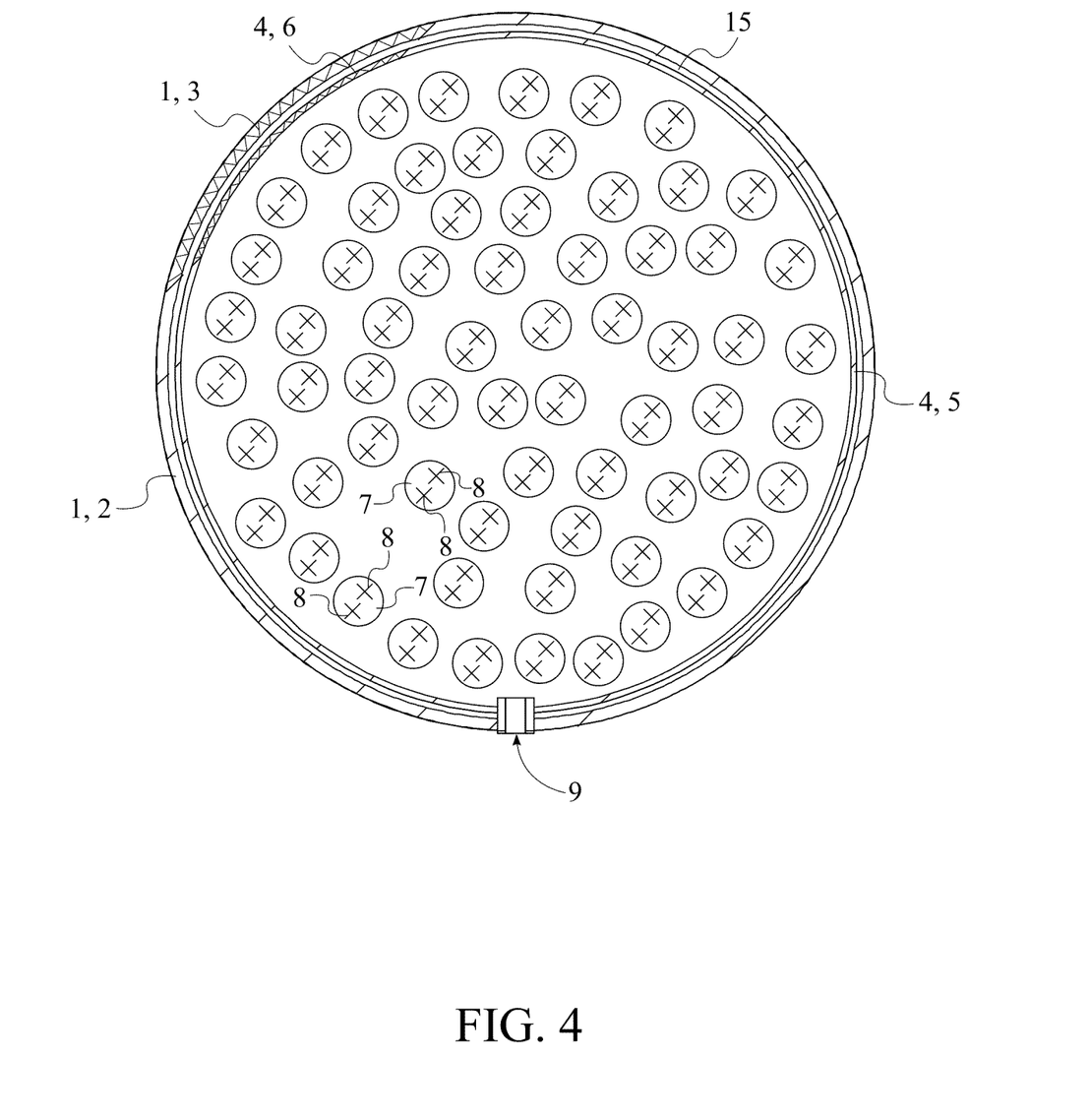
FIG. 4 is a cross-sectional view of the present invention taken along line 4-4 in FIG. 3 displaying the inner gas-permeable enclosure, the quantity of absorbent filling, and the quantity of aromatherapy fluid.
Figure 5:
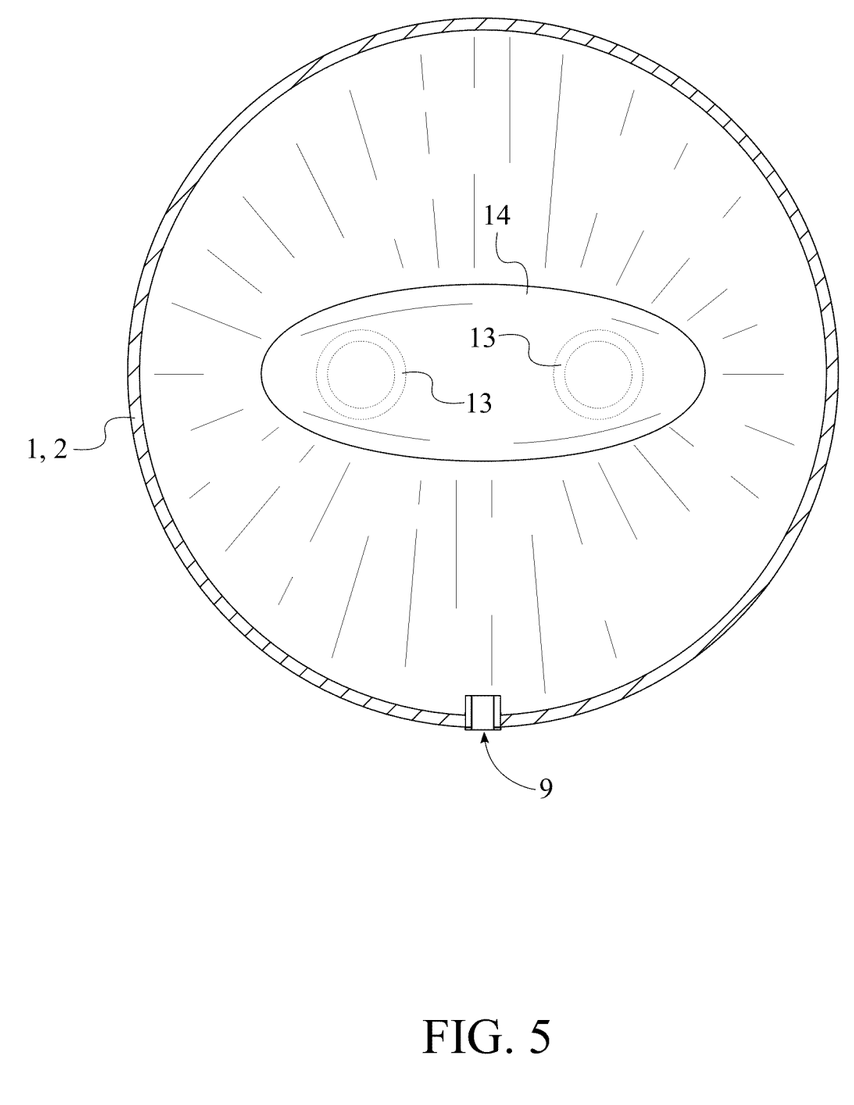
FIG. 5 is a cross-sectional view of the present invention taken along line 5-5 in FIG. 3 without the inner gas-permeable enclosure and displaying the reinforcement feature.

In order for the user to replenish the present invention with additional aromatherapy fluid 8 when the quantity of aromatherapy fluid 8 is running low or completely used up and with reference to FIG. 4, the present invention may further comprise a one-way valve 9. The one-way valve 9 traverses through the outer gas-permeable enclosure 1 and into the inner gas-permeable enclosure 4. More specifically and with reference to FIGS. 8 and 9, the one-way valve 9 is a bead valve that can establish a fluid communication between a refilling device and the inner gas-permeable enclosure 4 while still preventing the leak of the quantity of aromatherapy fluid 8. In more detail, the user can insert the refilling device, which is preferably a pipette, into the one-way valve 9 in order to replenish the present invention with additional aromatherapy fluid 8. The quantity of absorbent filling 7 is re-soaked with the aromatherapy fluid 8 through this process. In order to conceal the one-way valve 9, the present invention may further comprise a valve cover in order to selectively reveal or conceal the one-way valve 9.

Figure 6:
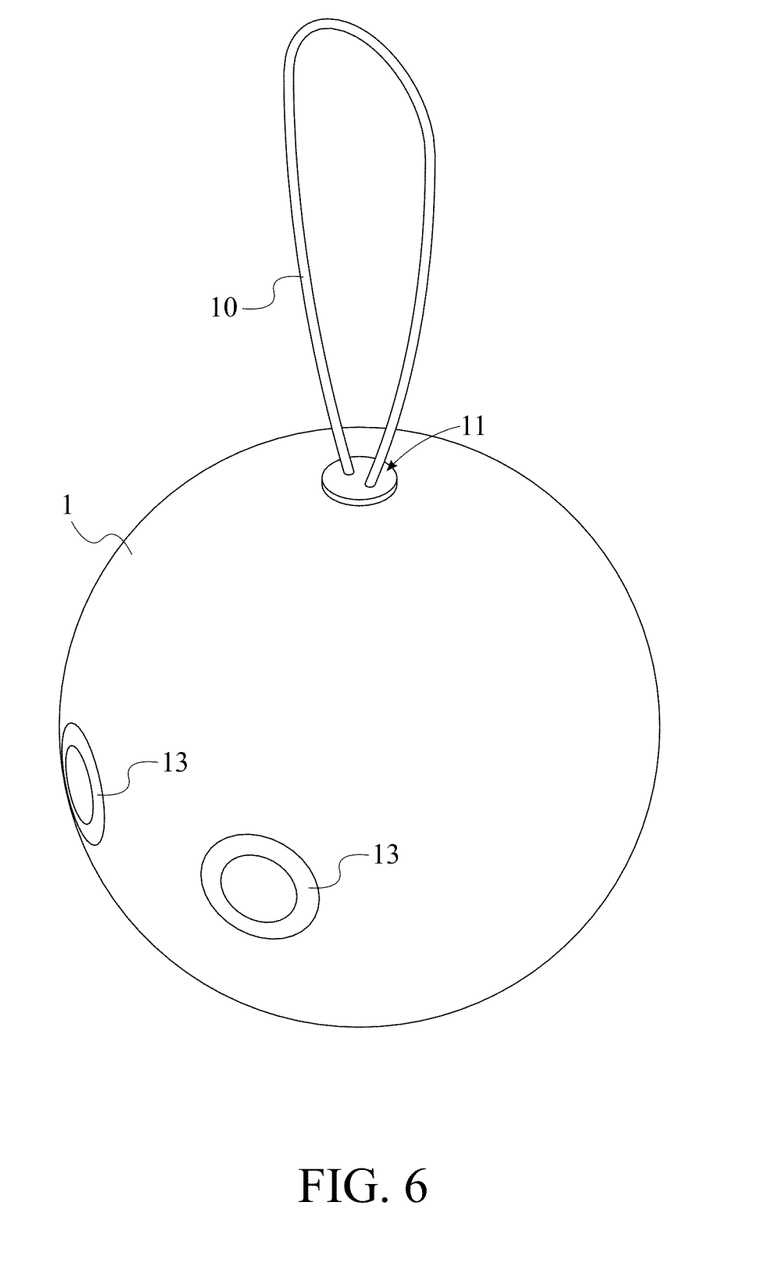
FIG. 6 is a top perspective view of the present invention displaying the lanyard.
Figure 7:
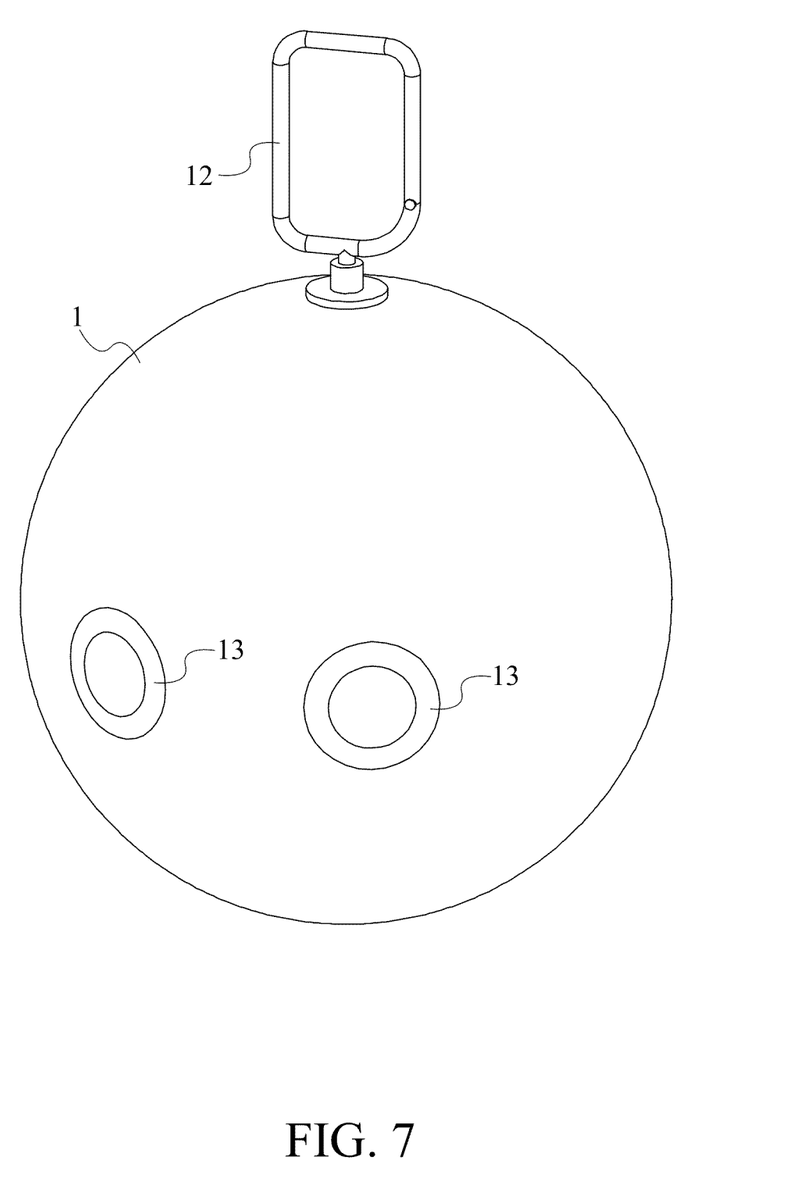
FIG. 7 is a front perspective view of the present invention displaying the clip.
Figure 8:
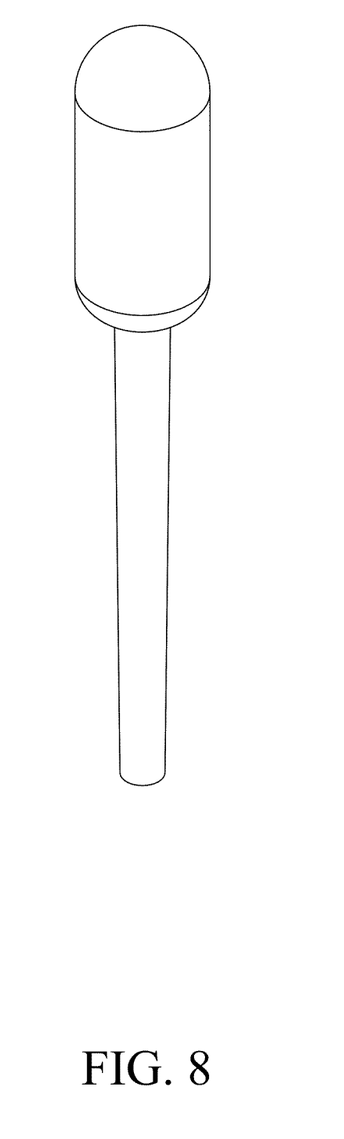
FIG. 8 is a top perspective view of the present invention displaying the refilling device.

In order to enable users to easily carry the outer-gas permeably enclosure without directly holding the outer gas-permeable enclosure 1 and with reference to FIG. 6, the present invention may further comprise a lanyard 10. The lanyard 10 comprise a fixed end 11 and the fixed end 11 is externally connected to the outer gas-permeable enclosure 1. Using the lanyard 10, the user can hang the present invention around his or her neck or the user can grasp the lanyard 10 in order to carry the present invention without directly holding the outer gas-permeable enclosure 1. Alternatively and with reference to FIG. 7, the present invention may further comprise a clip 12 instead of the lanyard 10. Similar to the lanyard 10, the clip 12 is externally connected to the outer gas-permeable enclosure 1. Using the clip 12, the user can attach the present invention onto his or her belt or pants, attach the present invention to a keychain loop, or the user can grasp the clip 12 in order to carry the present invention without directly holding the outer gas-permeable enclosure 1.

As the present invention is used over and over again, the quantity of absorbent filling 7 may decay over time. In order for the user to replace the quantity of absorbent filling 7 with reference to FIG. 4, the outer gas-permeable enclosure 1 comprises an outer enclosure body 2 and an outer access feature 3, and the inner gas-permeable enclosure 4 comprises an inner enclosure body 5 and an inner access feature 6. The outer access feature 3 is operatively integrated into the outer enclosure body 2 in order for the user to access the inner gas-permeable enclosure 4 within the outer enclosure body 2. In more detail, the outer access feature 3 is preferably fastening mechanism such as, but not limited to, a zipper, or a hook-and-loop fastener that can be unfastened for the user to access the interior of the outer gas-permeable enclosure 1. Similarly, the inner access feature 6 is operatively integrated into the inner enclosure body 5 in order for the user to access the quantity of absorbent filling 7 within the inner enclosure body 5. The inner access feature 6 is preferably a fastening mechanism such as, but not limited to, a zipper or a hook-and-loop fastener that can be unfastened for the user to access the interior of the inner gas-permeable enclosure 4. Further, the user can access the quantity of absorbent filling 7 in order to replace the quantity of absorbent filling 7 if needed.

In order to add an aesthetic feature to the present invention and with reference to FIG. 1, the present invention may further comprise at least one ornament 13. The at least one ornament 13 is externally connected to the outer gas-permeable enclosure 1. More specifically, the at least one ornament 13 is preferably stitched onto the outer gas-permeable enclosure 1. Although, various methods can be used to externally connect the at least one ornament 13 to the outer gas-permeable enclosure 1. The at least one ornament 13 may be various types of decorations such as those used on a stuffed animal. For example, the at least one ornament 13 is preferably a pair of toy eyes. In order to prevent the user from accidentally tearing or damaging the outer gas-permeable enclosure 1 while handling the at least one ornament 13, the present invention may further comprise a reinforcement feature 14. The reinforcement feature 14 is connected within the outer enclosure body 2, adjacent to the at least one ornament 13. More specifically and with reference to FIG. 5, the reinforcement feature 14 may be a tightly-woven fabric that is stitched to the inside of the outer gas-permeable enclosure 1. Thus, the outer gas-permeable enclosure 1 is reinforced in order to prevent accidental tearing or damage when the user is handling the at least one ornament 13.

Figure 9:
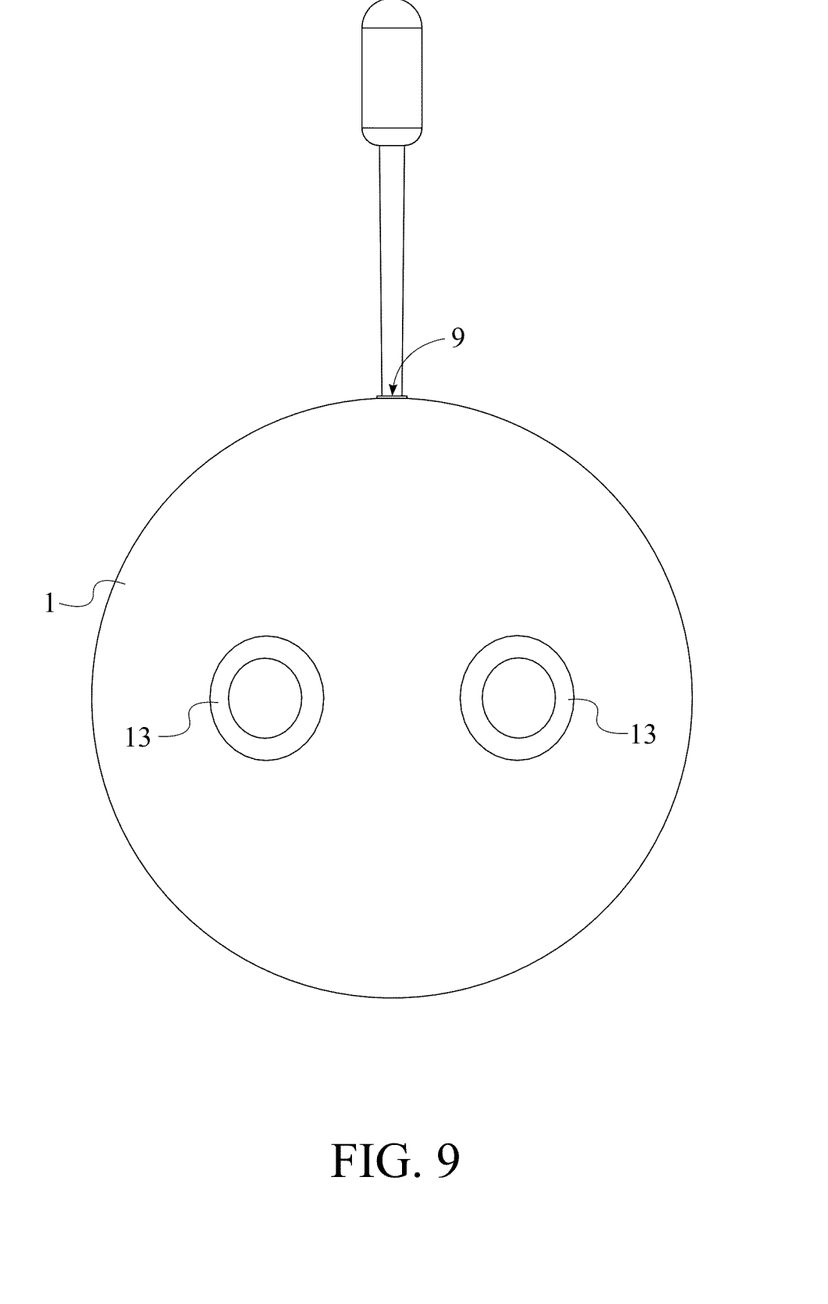
FIG. 9 is an upside-down front view of the present invention illustrating the replenishing of aromatherapy fluid.
Figure 10:
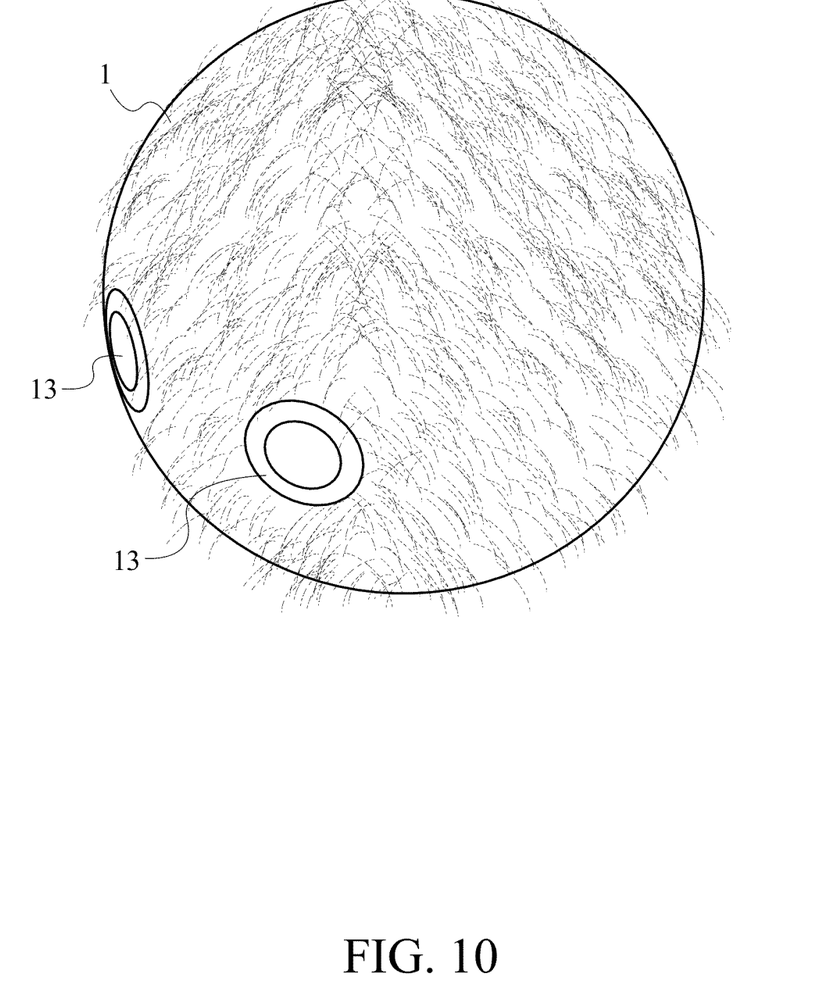
FIG. 10 is a top perspective view of the present invention showing the handheld body with fuzzy texture.

The present invention allows for exercises that cause the diffusing of the quantity of aromatherapy fluid 8 infused in the quantity of absorbent filling 7 within the inner gas-permeable enclosure 4 for aromatherapy. After each use, the user can replenish the aromatherapy fluid 8 by grabbing the refilling device and withdrawing an additional quantity of aromatherapy fluid 8 from a container using a pumping mechanism of the refiling device. The obtained aromatherapy fluid 8 is kept within a holding portion of the refilling device until ready to be dispensed. As can be seen in FIG. 9, the user inserts the refilling device into the one-way valve 9. The user dispenses the aromatherapy fluid 8 into the inner gas-permeable enclosure 4 where the quantity of absorbent filling 7 absorbs the dispensed aromatherapy fluid 8. The process can be repeated, as necessary.

Although the invention has been explained in relation to its preferred embodiment, it is to be understood that many other possible modifications and variations can be made without departing from the spirit and scope of the invention.

What is claimed is:
1. An aromatherapy sensory tool comprising:
an outer gas-permeable enclosure;
an inner gas-permeable enclosure;
a quantity of absorbent filling;
a quantity of aromatherapy fluid;
the quantity of absorbent filling being soaked with the quantity of aromatherapy fluid;
the quantity of absorbent filling being positioned within the inner gas-permeable enclosure;
the quantity of absorbent filling being rice;

the inner gas-permeable enclosure being positioned within the outer gas-permeable enclosure;

the outer gas-permeable enclosure and the inner gas-permeable enclosure being two hollow spherical bodies;

the outer gas-permeable enclosure and the inner gas-permeable enclosure being separated by a spherical gap;

the outer gas-permeable enclosure, the inner gas-permeable enclosure, and the spherical gap being positioned concentric with each other; and the outer gas-permeable enclosure being sized to be held in one hand.

2. The aromatherapy sensory tool as claimed in claim 1 further comprising:

a one-way valve;

the one-way valve traversing through the outer gas-permeable enclosure and into the inner gas-permeable enclosure;

the one-way valve being a bead valve; and the one-way valve being configured to refill the quantity of aromatherapy fluid into the inner gas-permeable enclosure by receiving a pipette through the one-way valve and into the inner gas-permeable enclosure.

3. The aromatherapy sensory tool as claimed in claim 1 further comprising:

a lanyard;

the lanyard comprising a fixed end; and the fixed end being externally connected to the outer gas-permeable enclosure.

4. The aromatherapy sensory tool as claimed in claim 1 further comprising:

a clip;

the clip being externally connected to the outer gas-permeable enclosure; and the clip being configured to suspend the outer gas-permeable enclosure.

5. The aromatherapy sensory tool as claimed in claim 1, wherein:

the outer gas-permeable enclosure comprises an outer enclosure body and an outer access feature;

the inner gas-permeable enclosure comprises an inner enclosure body and an inner access feature;

the outer access feature being operatively integrated into the outer enclosure body, wherein the outer access feature is used to access the inner gas-permeable enclosure within the outer enclosure body; and the inner access feature being operatively integrated into the inner enclosure body, wherein the inner access feature is used to access the quantity of absorbent filling within the inner enclosure body.

6. The aromatherapy sensory tool as claimed in claim 1 further comprising:

at least one ornament;

the at least one ornament being a pair of toy eyes;

the at least one ornament being externally connected to an outer surface of the outer gas-permeable enclosure.

7. The aromatherapy sensory tool as claimed in claim 6 further comprising:

a reinforcement feature;

the reinforcement feature being a tightly-woven fabric;

the reinforcement feature being stitched within the outer gas-permeable enclosure, adjacent to the at least one ornament; and the reinforcement feature being configured to structurally support the at least one ornament on the outer gas-permeable enclosure.

8. The aromatherapy sensory tool as claimed in claim 1, wherein the outer gas-permeable enclosure is made of a tactilely soft material.

9. The aromatherapy sensory tool as claimed in claim 1, wherein the inner gas-permeable enclosure is made of a fabric material.

10. The aromatherapy sensory tool as claimed in claim 1, wherein the quantity of aromatherapy fluid is an essential oil.

11. An aromatherapy sensory tool comprising:

an outer gas-permeable enclosure;

an inner gas-permeable enclosure;

a quantity of absorbent filling;

a quantity of aromatherapy fluid;

a one-way valve;

at least one ornament;

a reinforcement feature;

the outer gas-permeable enclosure comprises an outer enclosure body and an outer access feature;

the inner gas-permeable enclosure comprises an inner enclosure body and an inner access feature;

the outer gas-permeable enclosure being made of a tactilely soft material;

the quantity of absorbent filling being soaked with the quantity of aromatherapy fluid;

the quantity of absorbent filling being positioned within the inner pouch; gas-permeable enclosure;

the quantity of absorbent filling being rice;

the inner gas-permeable enclosure being positioned within the outer gas-permeable enclosure;

the outer gas-permeable enclosure and the inner gas-permeable enclosure being two hollow spherical bodies;

the outer gas-permeable enclosure and the inner gas-permeable enclosure being separated by a spherical gap;

the outer gas-permeable enclosure, the inner gas-permeable enclosure, and the spherical gap being positioned concentric with each other;

the outer gas-permeable enclosure being sized to be held in one hand;

the one-way valve traversing through the outer gas-permeable enclosure and into the inner gas-permeable enclosure;

the one-way valve being a bead valve;

the one-way valve being configured to refill the quantity of aromatherapy fluid into the inner gas-permeable enclosure by receiving a pipette through the one-way valve and into the inner gas-permeable enclosure;

the at least one ornament being a pair of toy eyes;

the at least one ornament being externally connected onto an outer surface of the outer gas-permeable enclosure;

the reinforcement feature being a tightly-woven fabric;

the reinforcement feature being stitched within the outer enclosure body, adjacent to the at least one ornament;

the reinforcement feature being configured to structurally support the at least one ornament on the outer gas-permeable enclosure;

the outer access feature being operatively integrated into the outer enclosure body, wherein the outer access feature is used to access the inner gas-permeable enclosure within the outer enclosure body; and the inner access feature being operatively integrated into the inner enclosure body, wherein the inner access feature is used to access the quantity of absorbent filling within the inner enclosure body.

12. The aromatherapy sensory tool as claimed in claim 11 further comprising:
- a lanyard;
- the lanyard comprises a fixed end; and
- the fixed end being externally connected to the outer gas-permeable enclosure.

13. The aromatherapy sensory tool as claimed in claim 11 further comprising:
- a clip;
- the clip being externally connected to the outer gas-permeable enclosure; and
- the clip being configured to suspend the outer gas-permeable enclosure.

14. The aromatherapy sensory tool as claimed in claim 11, wherein the inner gas-permeable enclosure is made of a fabric material.

15. The aromatherapy sensory tool as claimed in claim 11, wherein the quantity of aromatherapy fluid is an essential oil.

* * * * *